(12) United States Patent
Horner et al.

(10) Patent No.: US 8,623,018 B2
(45) Date of Patent: Jan. 7, 2014

(54) SEALING PLATE TEMPERATURE CONTROL

(75) Inventors: Glenn A. Horner, Boulder, CO (US); Christina A. Oliver, Longmont, CA (US); Kim V. Brandt, Loveland, CO (US)

(73) Assignee: Covidien LP, Mansfield, MA (US)

( * ) Notice: Subject to any disclaimer, the term of this patent is extended or adjusted under 35 U.S.C. 154(b) by 901 days.

(21) Appl. No.: 12/759,551

(22) Filed: Apr. 13, 2010

(65) Prior Publication Data
US 2011/0251611 A1    Oct. 13, 2011

(51) Int. Cl.
*A61B 18/08* (2006.01)

(52) U.S. Cl.
USPC ............................................. 606/51; 606/52

(58) Field of Classification Search
USPC .................................................. 606/27, 34, 41
See application file for complete search history.

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| D348,930 S | 7/1994 | Olson | |
| 5,647,871 A | 7/1997 | Levine et al. | |
| D384,413 S | 9/1997 | Zlock et al. | |
| 5,891,142 A * | 4/1999 | Eggers et al. | 606/51 |
| D424,694 S | 5/2000 | Tetzlaff et al. | |
| D425,201 S | 5/2000 | Tetzlaff et al. | |
| 6,174,309 B1 * | 1/2001 | Wrublewski et al. | 606/45 |
| D449,886 S | 10/2001 | Tetzlaff et al. | |
| D457,958 S | 5/2002 | Dycus et al. | |
| D457,959 S | 5/2002 | Tetzlaff et al. | |
| 6,611,699 B2 * | 8/2003 | Messing | 600/372 |
| D493,888 S | 8/2004 | Reschke | |
| D496,997 S | 10/2004 | Dycus et al. | |
| D499,181 S | 11/2004 | Dycus et al. | |
| D509,297 S | 9/2005 | Wells | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,329,257 B2 | 2/2008 | Kanehira et al. | |
| D564,662 S | 3/2008 | Moses et al. | |

(Continued)

FOREIGN PATENT DOCUMENTS

| | | |
|---|---|---|
| CN | 201299462 Y | 9/2009 |
| DE | 2415263 | 10/1975 |

(Continued)

OTHER PUBLICATIONS

U.S. Appl. No. 09/387,883, filed Sep. 1, 1999.

(Continued)

*Primary Examiner* — Michael Peffley
*Assistant Examiner* — Daniel Fowler (57) ABSTRACT

An end effector assembly for use with an electrosurgical instrument is provided. The end effector assembly has a pair of opposing jaw members. At least one of the jaw members has a support base and a sealing plate coupled to the electrical jaw lead. The sealing plate has a stainless steel layer and a copper layer formed on the underside of the stainless steel layer.

18 Claims, 6 Drawing Sheets

(56) References Cited

U.S. PATENT DOCUMENTS

| | | | |
|---|---|---|---|
| D567,943 S | 4/2008 | Moses et al. | |
| D575,395 S | 8/2008 | Hushka | |
| D575,401 S | 8/2008 | Hixson et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 8,112,871 B2* | 2/2012 | Brandt et al. | 29/592.1 |
| 2003/0139741 A1 | 7/2003 | Goble et al. | |
| 2003/0171747 A1 | 9/2003 | Kanehira et al. | |
| 2005/0033278 A1 | 2/2005 | McClurken et al. | |
| 2007/0173814 A1* | 7/2007 | Hixson et al. | 606/51 |
| 2007/0208341 A1* | 9/2007 | Kirwan | 606/51 |
| 2009/0112200 A1 | 4/2009 | Eggers | |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 02617 | 12/2005 |
| DE | 20 2007 00931 | 10/2007 |
| DE | 19738457 | 1/2009 |
| EP | 1159926 | 12/2001 |
| EP | 1772109 A1 | 4/2007 |
| EP | 1920752 A2 | 5/2008 |
| EP | 2147649 A1 | 1/2010 |
| EP | 2301467 A1 | 3/2011 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 99/40861 | 8/1999 |
| WO | WO 00/36986 | 6/2000 |
| WO | WO 01/54604 | 8/2001 |
| WO | WO 2005/0110264 | 11/2005 |

OTHER PUBLICATIONS

U.S. Appl. No. 09/591,328, filed Jun. 9, 2000.
U.S. Appl. No. 10/246,087, filed Sep. 17, 2002.
U.S. Appl. No. 12/336,970, filed Dec. 17, 2008.
U.S. Appl. No. 12/410,195, filed Mar. 24, 2009.
U.S. Appl. No. 12/441,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/665,081, filed Dec. 17, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/762,482, filed Apr. 19, 2010.
U.S. Appl. No. 12/766,476, filed Apr. 23, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/820,024, filed Jun. 23, 2010.
U.S. Appl. No. 12/821,253, filed Jun. 23, 2010.
U.S. Appl. No. 12/832,772, filed Jul. 8, 2010.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

(56) References Cited

OTHER PUBLICATIONS

Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.

(56) References Cited

OTHER PUBLICATIONS

Int'l Search Report EP 06020574.7 dated Oct. 2, 2007.
Intl Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Intl Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report mailed Jun. 30, 2011 in counterpart EP Application No. 11161117.4.

\* cited by examiner

SEALING PLATE TEMPERATURE CONTROL

BACKGROUND

1. Technical Field

The present disclosure relates to an electrosurgical instrument and method for sealing tissue. More particularly, the present disclosure relates to an electrosurgical tool including a jaw member having a sealing plate with improved temperature control.

2. Background of the Related Art

Electrosurgical forceps utilize mechanical clamping action along with electrical energy to effect hemostasis on the clamped tissue. The forceps (open, laparoscopic or endoscopic) often include electrosurgical sealing plates which apply the electrosurgical energy to the clamped tissue. By controlling the intensity, frequency and duration of the electrosurgical energy applied through the sealing plates to the tissue, the surgeon can coagulate, cauterize, and/or seal tissue.

During an electrosurgical procedure sealing plates may be used to apply electrosurgical energy or heat to tissue. Most sealing plates do not distribute heat evenly across the plates leading to hot zones within the sealing plates. Because the heat is not distributed evenly, the sealing procedure may take longer and may result in lower quality seal. Further, when energy is applied to the sealing plate, the sealing plate heats up. When energy is no longer applied, enough heat does not dissipate from the sealing plate, thereby causing heat to accumulate during subsequent applications of energy during an electrosurgical procedure resulting in a higher than desired temperature for the sealing plate.

SUMMARY

In an embodiment of the present disclosure, an end effector assembly including a pair of opposing jaw members is provided. At least one of the jaw members includes a support base and a sealing plate coupled to the electrical jaw lead. The sealing plate has a stainless steel layer and a copper layer formed on the underside of the stainless steel layer.

In another embodiment of the present disclosure, an electrosurgical instrument for sealing tissue is provided. The electrosurgical instrument may include a housing, a handle assembly, a rotating assembly, a trigger assembly, and an end effector assembly including a pair of opposing jaw members. Each of the jaw members includes a support base, an electrical jaw lead, and a sealing plate coupled to the electrical jaw lead. The sealing plate has a stainless steel layer and a copper layer formed on the underside of the stainless steel layer.

In yet another embodiment of the present disclosure another electrosurgical instrument for sealing tissue is provided. The electrosurgical instrument may include a pair of opposing shafts with each shaft having a handle at the proximal end of the shaft. The instrument may also include an end effector assembly including a pair of opposing jaw members attached at a distal end of the pair of opposing shafts wherein the opposing jaw members move from a first position to a second position by moving the pair of opposing shafts relative to one another. At least one of the jaw members includes a support base, an electrical jaw lead, and a sealing plate coupled to the electrical jaw lead. The sealing plate has a stainless steel layer and a copper layer formed on the underside of the stainless steel layer.

Each of the jaw members in the end effector assembly may have an insulative plate between the support base and the sealing plate. The electrical jaw lead may be coupled to the sealing plate with an ultrasonic weld or more specifically, coupled to the copper layer with an ultrasonic weld. The copper layer may be bonded to the stainless steel layer by cladding.

In yet another embodiment, the copper layer is formed on a portion of the underside of the stainless steel layer.

In yet another embodiment of the present disclosure, a method for constructing a jaw member of an end effector assembly is provided. The method may include forming a seal plate having a stainless steel layer and copper layer formed on an underside of the stainless steel layer, affixing the seal plate atop an insulative plate and affixing the seal plate and the insulative plate atop a support base. The seal plate, the insulative plate and the support base may be encapsulated by an outer insulative housing by an overmolding process.

Further the seal plate, insulative plate and support bases are affixed together by a snap-fit, over-molding, stamping or ultrasonically welded.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus that is closer to the user and the term "distal" refers to the end of the apparatus that is further away from the user. The term "clinician" refers to any medical professional (i.e., doctor, surgeon, nurse, or the like) performing a medical procedure involving the use of embodiments described herein.

As described in more detail below with reference to the accompanying figures, the present disclosure is directed to a jaw member of a vessel sealer having a sealing plate with a clad copper bottom layer. Having a copper layer below the sealing plate has many advantages. Copper conducts heat better than most other metals. Because it is a good heat conductor, copper provides for a more even distribution of heat, thereby providing a faster seal and reducing charring of tissue. Further, the copper layer reduces hot spots in the sealing plate by distributing heat across all areas of the sealing plate.

The copper layer may also act as a heat sink allowing for a more precise temperature control of the vessel sealer. For example, in between applications of energy, stainless steel sealing plates tend to dissipate heat at a slow rate. Therefore, during subsequent applications of energy, the amount of heat in the sealing plate accumulates, thereby leading to a higher than desired temperature for the sealing plates. Providing a layer of copper as a heat sink would cause the heat to dissipate at a faster rate, thereby preventing heat from accumulating and allowing for a more precise temperature control for the vessel sealer.

Figure 1:
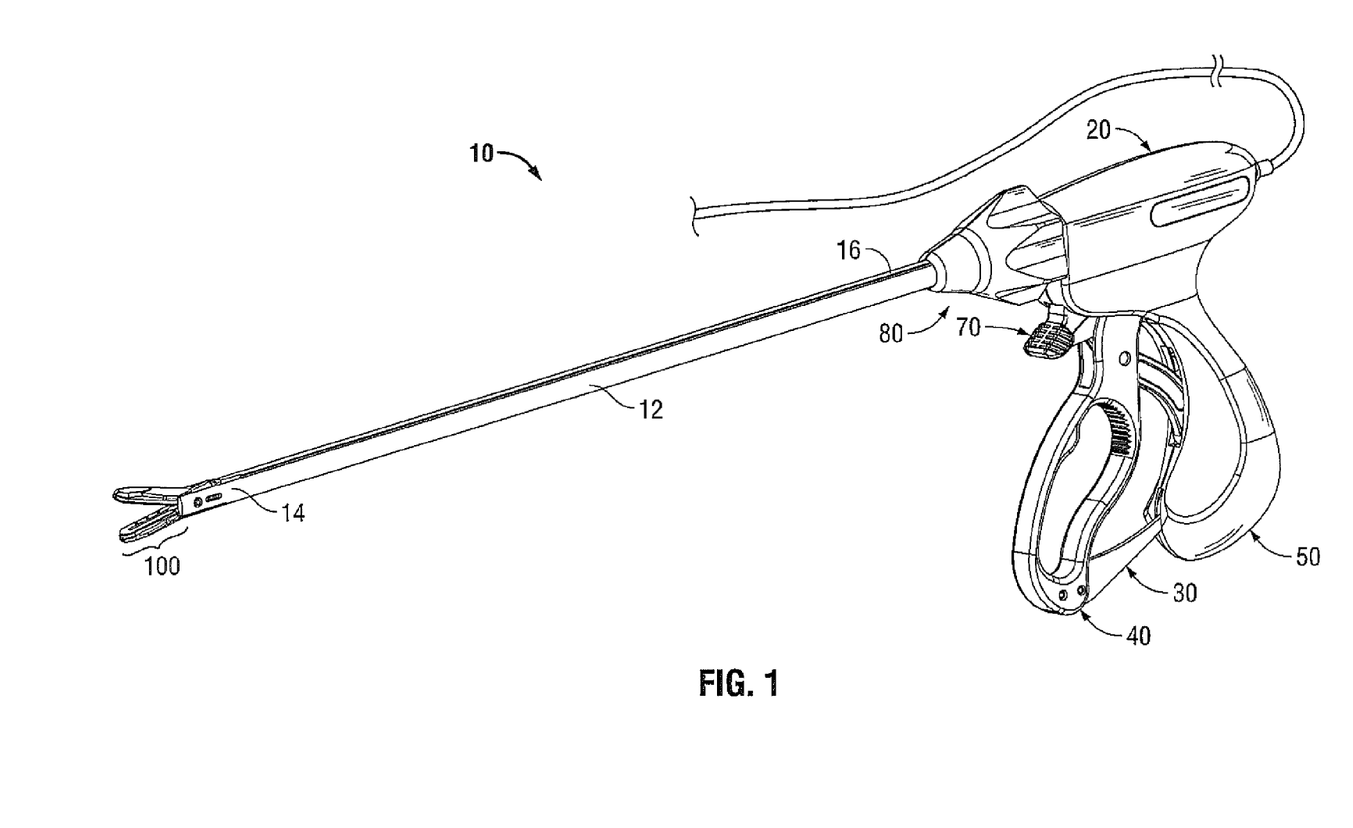
FIG. 1 is a perspective view of an endoscopic bipolar forceps in accordance with an embodiment of the present disclosure.

Turning to FIG. 1, an instrument generally identified as forceps 10 is for use with various surgical procedures and includes a housing 20, a handle assembly 30, a rotating assembly 80, a trigger assembly 70, and an end effector assembly 100 that mutually cooperate to grasp, seal, and divide tubular vessels and vascular tissues. Forceps 10 includes a shaft 12 that has a distal end 16 dimensioned to mechanically engage the end effector assembly 100 and a proximal end 14 that mechanically engages the housing 20. The end effector assembly 100 includes opposing jaw members 110 and 120, which cooperate to effectively grasp tissue for sealing purposes. The end effector assembly 100 is a bilateral assembly, i.e., both jaw members 110 and 120 pivot relative to one another about a pivot pin 95. The jaw members 110 and 120 are curved to facilitate manipulation of tissue and to provide better "line of sight" for accessing targeted tissues.

Examples of forceps are shown and described in commonly-owned U.S. application Ser. No. 10/369,894 entitled "VESSEL SEALER AND DIVIDER AND METHOD MANUFACTURING SAME" and commonly owned U.S. application Ser. No. 10/460,926 (now U.S. Pat. No. 7,156,846) entitled "VESSEL SEALER AND DIVIDER FOR USE WITH SMALL TROCARS AND CANNULAS.

Figure 2:
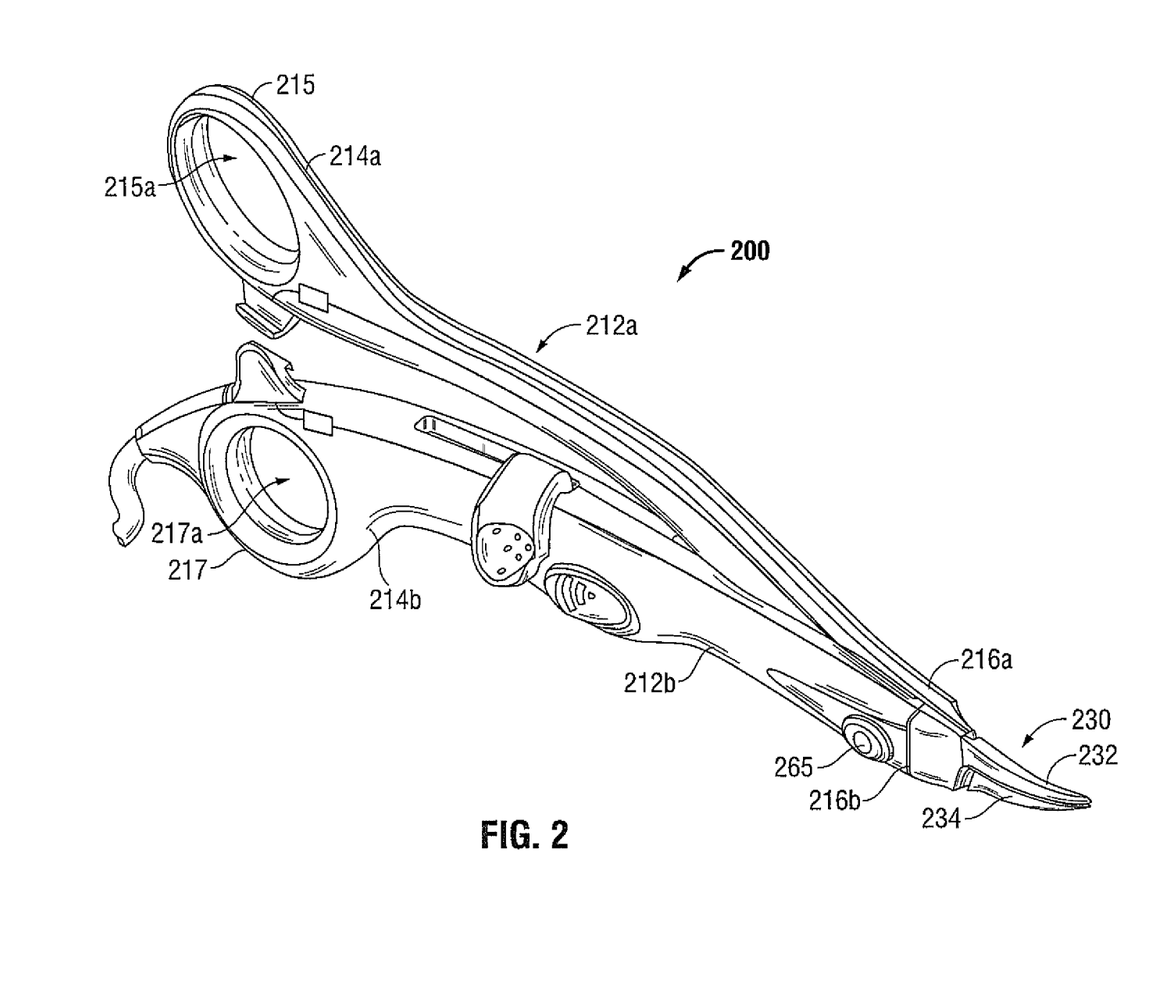
FIG. 2 is a perspective view of an open bipolar forceps in accordance with an embodiment of the present disclosure.

With regard to FIG. 2, an open forceps 200 for use with various surgical procedures is shown. Forceps 200 includes a pair of opposing shafts 212a and 212b having an end effector assembly 230 attached to the distal ends 216a and 216b thereof, respectively. End effector assembly 230 is similar in design to end effector assembly 100 and includes pair of opposing jaw members 232 and 234 that are pivotably connected about a pivot pin 265 and which are movable relative to one another to grasp tissue. Each shaft 212a and 212b includes a handle 215 and 217, respectively, disposed at the proximal end 214a and 214b thereof which each define a finger hole 215a and 217a, respectively, therethrough for receiving a finger of the user. Finger holes 215a and 217a facilitate movement of the shafts 212a and 212b relative to one another which, in turn, pivot the jaw members 232 and 234 from an open position wherein the jaw members 232 and 234 are disposed in spaced relation relative to one another to a clamping or closed position wherein the jaw members 232 and 234 cooperate to grasp tissue therebetween.

Figure 3A:
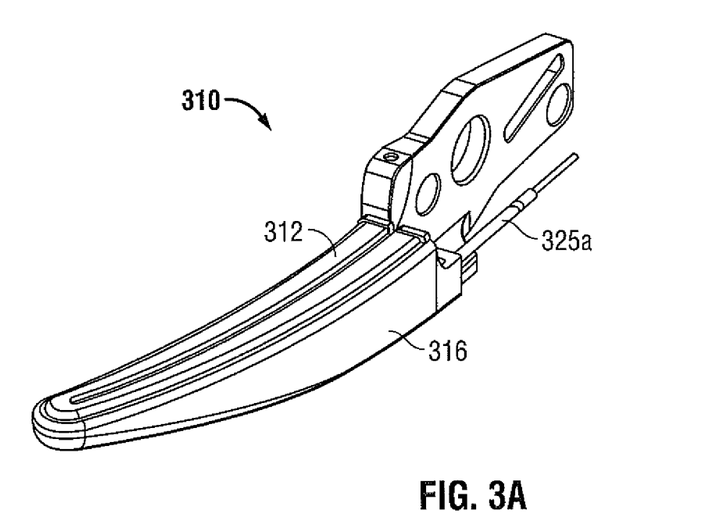
FIGS. 3A and 3B are perspective views of opposing jaw members according to an embodiment of the present disclosure.
Figure 3B:
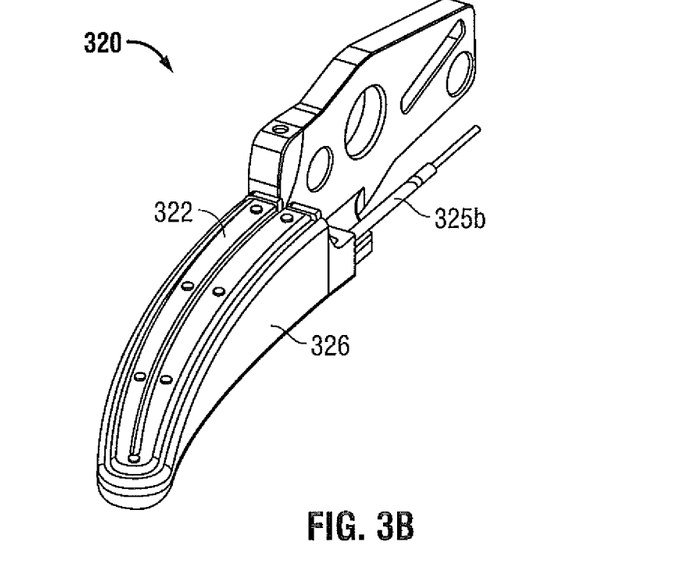

FIGS. 3A and 3B are perspective views of opposing jaw members 310 and 320 according to one embodiment of the present disclosure. Each of the jaw members 310 and 320 include: sealing plates 312 and 322, respectively; electrical jaw leads 325a and 325b, respectively; and outer insulative housings 316 and 326 formed as plastic overmolds. Electrical jaw leads 325a and 325b supply energy to at least one of the opposing jaw members 310 and 320. In some embodiment, only one of the jaw members has a seal plate and the other jaw member is a monolithic jaw with a seal surface.

Figure 4A:
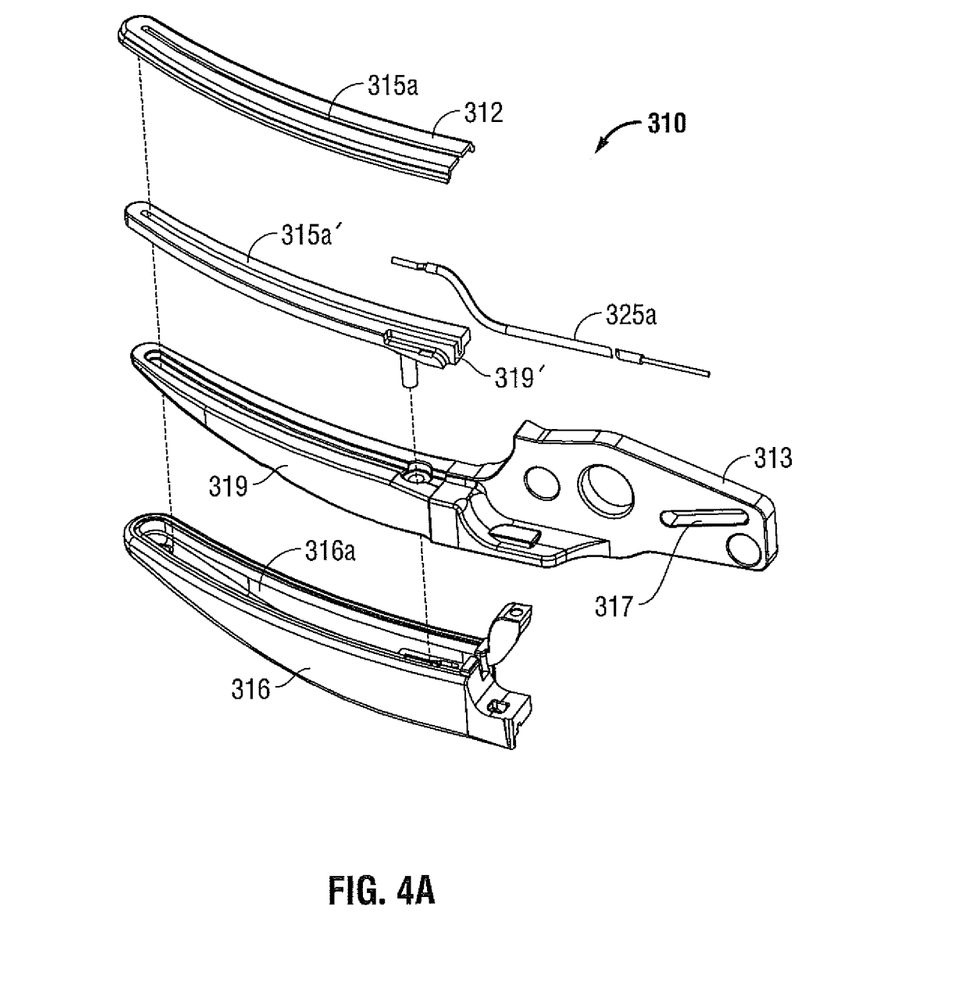
FIGS. 4A and 4B are exploded views of the opposing jaw members of FIGS. 3A and 3B respectively.
Figure 4B:
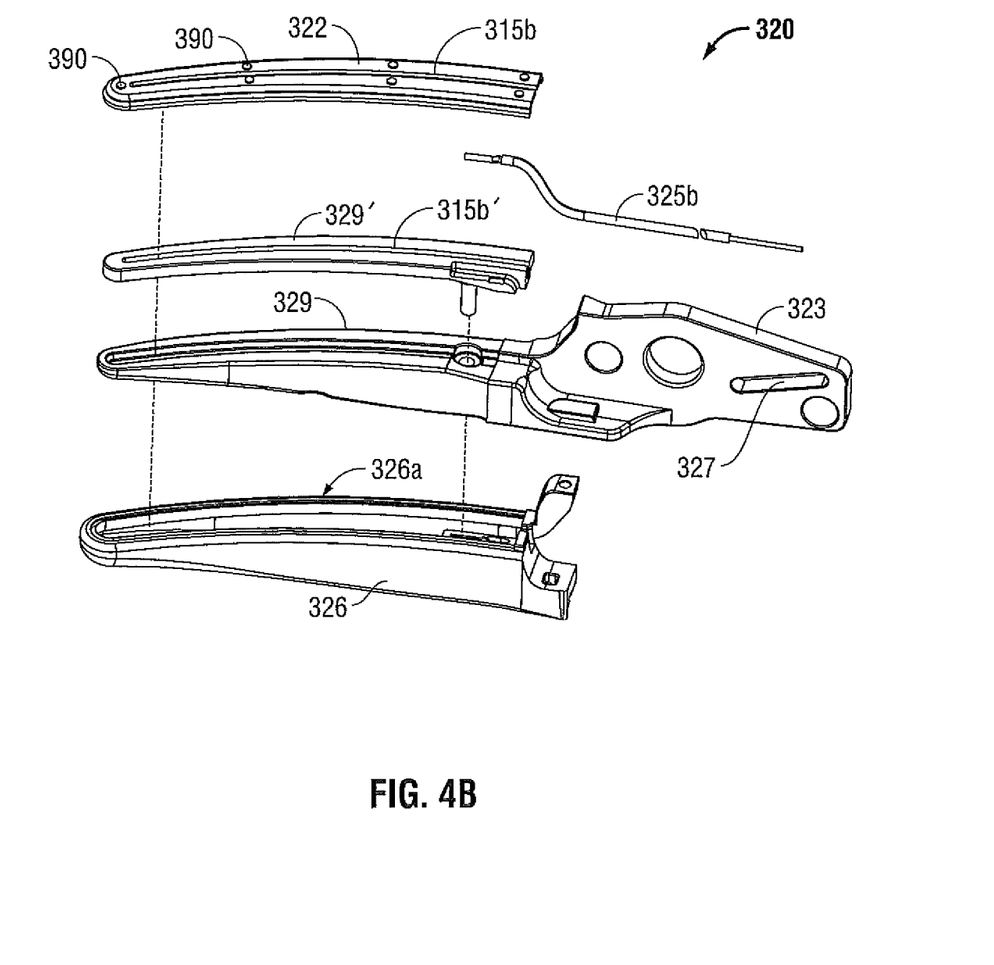

Turning to FIGS. 4A and 4B, the opposing jaw members 310 and 320 include support bases 319 and 329 that extend distally from flanges 313 and 323, respectively. The support bases 319 and 329 are dimensioned to support insulative plates 319' and 329', which in turn, support electrically conductive sealing plates 312 and 322 thereon. It is contemplated that sealing plates 312 and 322 may be affixed atop the insulative plates 319' and 329', respectively, and support bases 319 and 329, respectively, in any known manner in the art, snap-fit, over-molding, stamping, ultrasonically welded, etc. The support bases 319 and 329, insulative plates 319' and 329', and sealing plates 312 and 322 are encapsulated by the outer insulative housings 316 and 326 by way of a subsequent overmolding process. The jaw members 310 and 320 are connected via any suitable joining means to electrical jaw leads 325a and 325b, respectively.

The jaw members 310 and 320 also include proximal flanges 313 and 323 extending proximally from the support bases 319 and 329, respectively, each of which includes an elongated angled cam slot 317 and 327, respectively, defined therethrough. The jaw member 320 may also include a series of stop members 390 disposed on the inner facing surface of the electrically conductive sealing plate 312 to define a gap between opposing jaw members 310 and 320 during sealing and cutting of tissue. The series of stop members 390 are applied onto the sealing plate 312 during manufacturing. Likewise, the electrically conductive sealing plates 312 and 322 and the insulator plates 319' and 329' may include respective longitudinally-oriented knife slots 315a, 315a' and 315b, 315b', respectively, defined therethrough for reciprocation of the knife blade (not shown).

Figure 5:
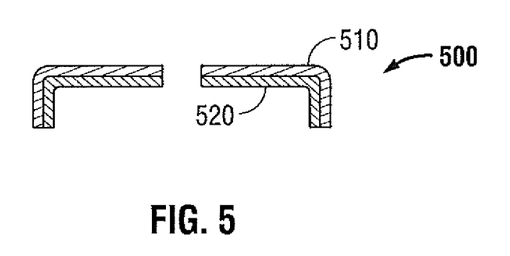
FIG. 5 is a cross sectional view of a sealing plate according to an embodiment of the present disclosure.

Turning to FIG. 5, a cross-sectional view of a sealing plate 500 is shown. Sealing plate 500 is similar to sealing plates 312 and 322 described above. As shown in FIG. 5, sealing plate 500 has a stainless steel layer 510 and copper layer 520 formed on an underside of the stainless steel layer 510. Sealing plate 500 may be formed by any suitable process such as cladding. Cladding is the bonding together of dissimilar metals. Cladding may be achieved by extruding two or more metals through a die as well as pressing, rolling or blasting sheets together under high pressure. Copper layer 520 may have a thickness ranging from 0.002 inches to 0.005 inches. Sealing plate 500, which includes stainless steel layer 510 and copper layer 520, may have a thickness ranging from 0.005 inches to 0.008 inches. As described above, adding the copper layer provides for better heat distribution and more precise temperature control for the vessel sealer. Sealing plate 500 may be formed by cladding a sheet of copper to a sheet of stainless steel. Once the two metal sheets are bonded together, sealing plate 500 may be formed by stamping, machining or any other suitable method that may be used to form a sealing plate.

Stainless steel layer 510 may have a polymer coating to prevent corrosion. The polymer coating may be applied by vapor deposition, heat treatment or any other suitable method that may be used to apply a coating to stainless steel layer 510.

Electrical jaw leads 325a and 325b are joined to a copper layer 520 via any suitable joining method. Ultrasonic welding of electrical jaw leads 325a and 325b to copper layer 520 may allow for a better connection as well as a faster manufacturing method of attaching the wire via crimping.

Figure 6A:
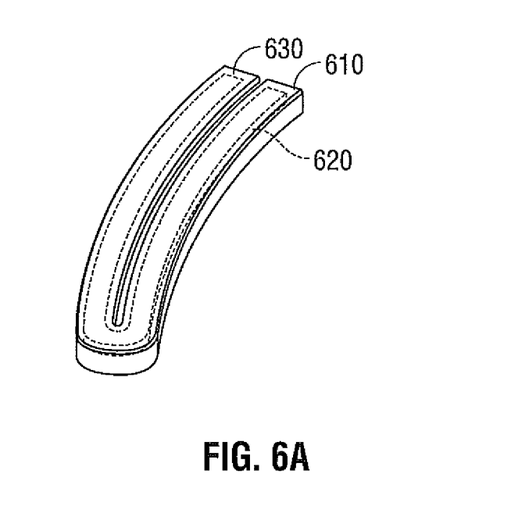
FIG. 6A is a perspective view of a sealing plate according to another embodiment of the present disclosure.
Figure 6B:
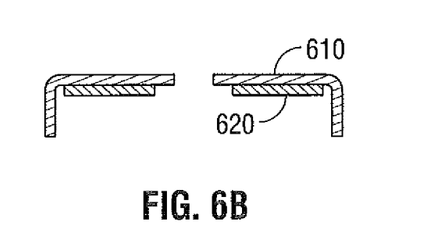
FIG. 6B is a cross-sectional view of the sealing plate of FIG. 6A.

Turning to FIGS. 6A and 6B, a sealing plate according to another embodiment of the present disclosure is shown generally as 600. As shown in FIGS. 6A and 6B, sealing plate 600 includes a stainless steel layer 610 and a copper layer 620. Copper layer 620 partially covers stainless steel layer 610. Sealing plate 600 may be formed as described above by cladding a sheet of copper to a sheet of stainless steel and then stamping out or machining the bonded sheets into the shape of a sealing plate. Then a photolithography procedure may be used to etch portions of the copper from the edges of the sealing plate 600 leaving a heating section 630. By etching out the copper from sealing plate 600, only heating section 630 applies heat to tissue during a vessel sealing procedure. By not applying heat along the edges of sealing plate 600, charring of tissue during a vessel sealing procedure may be reduced.

Although embodiments of the present disclosure have been described above using specific examples, other materials and methods may be used to achieve temperature control for a sealing plate. For instance, instead of copper, a layer of gold, silver or diamond may be used to distribute evenly along the sealing plate. Further, other methods may be used to bond copper to stainless steel such as electroplating, vapor deposition, welding, brazing, soldering, adhesive bonding, chemical bonding or any other manufacturing process that may be used to bond two dissimilar metals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. An end effector assembly including a pair of opposing jaw members, at least one of the jaw members comprising:
   a support base configured to support a sealing plate having a knife channel defined therethrough, wherein the sealing plate includes a stainless steel layer and a copper layer formed on a portion of an underside of the stainless steel layer, the copper layer being recessed from the knife channel to evenly distribute and transfer heat to the portion of the stainless steel layer; and
   an outer insulative housing configured to encapsulate an entire length of the support base.

2. The end effector assembly according to claim 1, wherein each of the jaw members further comprises an insulative plate between the support base and the sealing plate.

3. The end effector assembly according to claim 1, further comprising an electrical jaw lead coupled to the sealing plate with a weld.

4. The end effector assembly according to claim 3, wherein the electrical jaw lead is ultrasonically welded to the copper layer of the sealing plate.

5. The end effector assembly according to claim 1, wherein the copper layer is bonded to the stainless steel layer.

6. The end effector assembly according to claim 5, wherein the copper layer is cladded to the stainless steel layer.

7. The end effector assembly according to claim 1, wherein the copper layer includes a thickness ranging from 0.002 inches to 0.005 inches.

8. The end effector assembly according to claim 1, wherein the seal plate includes a thickness ranging from 0.005 inches to 0.008 inches.

9. The end effector assembly according to claim 1, wherein the stainless steel layer includes a polymer coating.

10. An electrosurgical instrument for sealing tissue, comprising:
    a housing;
    a handle assembly;
    a trigger assembly; and
    an end effector assembly including a pair of opposing jaw members, each of the jaw members comprising:
       a support base configured to support a sealing plate having a knife channel defined therethrough;
       an electrical jaw lead coupled to the sealing plate, wherein the sealing plate includes a stainless steel layer and a copper layer formed on a portion of an underside of the stainless steel layer, the copper layer being recessed from the knife channel to evenly distribute and transfer heat to the portion of the stainless steel layer; and
       an outer insulative housing configured to encapsulate an entire length of the support base.

11. The electrosurgical instrument according to claim 10, wherein each of the jaw members further comprises an insulative plate between the support base and the sealing plate.

12. The electrosurgical instrument according to claim 10, wherein the electrical jaw lead is coupled to the sealing plate with a weld.

13. The electrosurgical instrument according to claim 10, wherein the electrical jaw lead is ultrasonically welded to the copper layer of the sealing plate.

14. The electrosurgical instrument according to claim 10, wherein the copper layer is bonded to the stainless steel layer.

15. The electrosurgical instrument according to claim 14, wherein the copper layer is cladded to the stainless steel layer.

16. An electrosurgical instrument for sealing tissue, comprising:
    a pair of opposing shafts, each shaft having a handle at the proximal end of the shaft; and
    an end effector assembly including a pair of opposing jaw members attached at a distal end of the pair of opposing shafts wherein the opposing jaw members move from a first position to a second position by moving the pair of opposing shafts relative to one another, at least one of the jaw members comprising:
       a support base configured to support a sealing plate;
       an electrical jaw lead coupled to the sealing plate; and
       a sealing plate coupled to the electrical jaw lead, wherein the sealing plate includes a stainless steel layer and a copper layer formed on a portion of an underside of the stainless steel layer; and
       an outer insulative housing configured to encapsulate an entire length of the support base.

17. A method for constructing a jaw member of an end effector assembly, comprising:
    forming a seal plate having a stainless steel layer and copper layer formed on a portion of an underside of the stainless steel layer;
    affixing the seal plate atop an insulative plate;
    affixing the seal plate and the insulative plate atop a support base;
    encapsulating the seal plate, the insulative plate and the support base by an outer insulative housing by an overmolding process such that and entire length of the support base is encapsulated by the outer insulative housing.

18. The method according to claim 17, wherein the seal plate, insulative plate and support bases are affixed together by a snap-fit, over-molding, stamping or ultrasonically welded.

* * * * *